United States Patent [19]

Coenen et al.

[11] 4,255,356

[45] Mar. 10, 1981

[54] PURIFICATION OF TERTIARY AMINES USING AN ADSORBENT

[75] Inventors: Alfred Coenen; Kurt Kosswig, both of Marl; Ferdinand Von Praun, Haltern; Hans-Peter Schüller, Marl, all of Fed. Rep. of Germany

[73] Assignee: Chemische Werke Hüls AG, Marl, Fed. Rep. of Germany

[21] Appl. No.: 64,808

[22] Filed: Aug. 8, 1979

[51] Int. Cl.$^3$ .............................................. C07C 85/26
[52] U.S. Cl. .................................................. 564/499
[58] Field of Search ................................... 260/583 N

[56]   References Cited
U.S. PATENT DOCUMENTS

| 3,406,204 | 10/1968 | Bathellier et al. | ............... 260/583 N |
| 3,855,298 | 12/1974 | Bathellier et al. | ............... 260/583 N |

*Primary Examiner*—John Doll
*Attorney, Agent, or Firm*—Gilbert L. Wells

[57]   ABSTRACT

A method of purifying tertiary amines by removing sec. and prim. amines and/or their hydrochlorides produced in the manufacture of the tertiary amines. The impurities are removed by dissolving the impure tertiary amines in an organic solvent and the resulting solution is passed over absorbents such as aluminum oxides having a specific surface area of about 100 to 400 square meters per gram. The sec. and prim. amines and/or their hydrochlorides are retained on the adsorbents and pure tertiary amines are useful in the solvents or can be separated therefrom. The adsorbents are regenerated by passing polar solvents thereover to remove the sec. and prim. amines and/or their hydrochlorides.

12 Claims, No Drawings

PURIFICATION OF TERTIARY AMINES USING AN ADSORBENT

CROSS-REFERENCES TO RELATED APPLICATIONS

The disclosures of Assignee's copending U.S. Pat. application of Alfred Coenen et al. entitled "Method of Manufacturing Hydrogen Chloride From Solutions of Amine Hydrochlorides" filed Feb. 6, 1979 and having Ser. No. 10,048 and U.S. Pat. application of Alfred Coenen et al. entitled "Method for Obtaining Gaseous Hydrogen Chloride from Dilute Aqueous Hyrochloric Acid" filed Aug. 8, 1979 having Ser. No. 64,633 are incorporated herein.

BACKGROUND OF THE INVENTION

The field of the invention is the purification of tertiary amines and the present invention is particularly concerned with elution (separation by washing) of adsorbents with the tertiary amines dissolved in an eluent (organic solvent) followed by separation of the tertiary amines from the eluate (washing obtained by elution).

Both in the preparation of tertiary amines and in their exposure to heat in certain industrial processes, undesired by-products are formed in most cases. Their complete removal by preparative methods is either involved or impossible.

The tertiary amines being purified in the present invention are obtained, for example, from the methods of manufacture as disclosed in the Kirk-Othmer, "Encyclopedia of Chemical Technology," 2nd edition, vol. 2 (1963) pages 97-127, particularly pages 117 and 125 where the preparation of tertiary amines is disclosed and from the thermolysis of tertiary amine hydrochlorides such as is described, for example, in West German published application No. 2,633,640and in U.S. Pat. application Ser. No. 10,048.

The process of West German published application No. 2,633,640 is carried out with the following steps:

(a) aqueous hydrochloric acid is extracted with an amine or a mixture of an amine and an inert, water-immiscible solvent which boils below the amine used, the latter being tertiary alkylamines, tertiary aryldialkylamines, secondary arylalkyamines, primary alkylarylamines or mixtures thereof, which contain 14 to 36 carbon atoms in the nitrogen-bonded side chains, which side chains include at most one nitrogen-bonded methyl group and at least one aliphatic radical containing at least 6carbon atoms, the acid constant $K_a$ of the amine being less than $10^{-3}$, (b) an inert, water-immiscible solvent which boils below the amine used is added to the extract, unless the solvent has already been added in stage (a), (c) the extract is distilled, the resulting vapors are condensed, the water is continuously removed from the two-phase condensate, and the organic phase is returned to the distillation process, and (d) after removing the water, the extract is distilled under reflux at temperatures of between 100° and 250° C. at the column bottom, and the gaseous hydrogen chloride liberated at the top of the column is taken off.

According to the method of U.S. Pat. application Ser. No. 10,048, which does not form part of the prior art, the gaseous hydrogen chloride is obtained—in a modification of the process of the West German published application—by heating the mixture of amine hyrochloride and solvent to a temperature below the boiling point of the solvent and separating off the hydrogen chloride liberated by passing an inert gas stream through the mixture.

It has been found, in the thermal cleavage of amine hydrochlorides, that tertiary amines decompose within a more or less brief period, inter alia with the formation of interfering primary and secondary amines, which amines in general also represent the essential part of the impurities encountered when tertiary amines are manufactured. These amines formed by degradation, and their hydrochlorides, must therefore also be removed before recycling the tertiary amines in order to improve the economy of the prior art processes.

SUMMARY OF THE INVENTION

It is therefore an object of the present invention to develop a method which permits the purification of tertiary amines in a simple and economical manner.

This overall object is achieved by passing the impure tertiary amines over absorbents so that the impurities are absorbed and isolating the pure tertiary amines.

When necessary, the amines to be purified are dissolved in organic solvents, the solution of amines is passed over absorbents and the pure tertiary amine is isolated from the purified solution.

In general, the procedure followed in the process according to the present invention is to pass the tertiary amine to be purified, preferably dissolved in a suitable organic solvent, over the adsorbent. An amine/solvent ratio of about 1:1 to about 1:10 is generally used.

The impurities are removed from the adsorbents to regenerate them by passing polar solvents thereover. The tertiary amines can be removed from the solvents by rectification.

DESCRIPTION OF THE PREFERRED EMBODIMENTS

Exemplary impure tertiary amine starting materials include tri-(2-ethylhexyl)-amine contaminated with di(2-ethylhexyl)-amine hydrochloride; tri-(2-ethylhexyl)-amine contaminated with di-(2-ethylhexyl)-amine and 2-ethylhexylamine; tri-(2-ethylhexyl)-amine contaminated with di-(2-ethylhexyl)-amine; trioctylamine contaminated with dioctylamine; triethylamine contaminated with diethylamine; trilaurylamine contaminated with dilaurylamine; trihexylamine contaminated with dihexylamine, tri-decylamine contaminated with didecylamine, trimyristylamine contaminated with dimyristylamine, tri-cetylamine contaminated with dicetylamine, tristearylamine contaminated with distearylamine.

The degree of purity of the tertiary amine in the starting material is usefully above 80%, preferably above 90%, and especially preferentially above 95%.

Suitable solvents are those which are entirely or substantially of non-polar character, such as, for example, straight-chain or branched aliphatic, cycloaliphatic, araliphatic or aromatic hydrocargbons. Typical examples of these groups of hydrocarbons are hexane, heptane, octane, iso-octane, nonane, decane, undecane, dodecane, tetradecane, cyclohexane, methylcyclohexane, decalin, tetralin, benzene, toluene, cumene, xylenes, cymenes, ethylbenzene, p-tert.-butyltoluene, trimethylbenzenes, 1,2,4-triethylbenzene, 1,3,4-triethylbenzene, tert.-butyl-m-xylene, 1,2,3,4-tetramethylbenzene, 1,2,3,5-tetramethylbenzene, 3-phenylpentane and dodecylbenzene.

The appropriate concentration of the tertiary amine in the solution depends on the nature of the amine and on the amount of the impurities to be removed and can easily be determined by a few exploratory tests. In general, an amine-solvent ratio of 1:1 to 1:10 is used. In addition, further solvents can be used as the eluant. It is also possible, where high concentrations of impurities are involved, to carry out a partial preliminary removal of these impurities by utilizing the differing solubilities in the chosen solvent.

Adsorbents suitable for the process according to the present invention are aluminum oxides of large specific surface area of about 100 to about 400 m$^2$/g in granular, tableted or crushed form. It has been found that the basicity of the aluminum oxide is not a deciding factor, and superficially basic, neutral or acidic aluminum oxide can be employed. On the other hand, the level of activity is important. Products with activity levels of 1 to 3, preferably activity levels 1 and 2, are useful. Aluminum oxide used as a chromatographic adsorbent is classified under 5 activity levels, according to the Brockmann scale. The aluminum oxides standaridized by the Brockmann method differ is respect to their water content which, in percent by weight, is as follows: 1 (0%), 2 (3%), 3 (4.5%), 4 (9.5%), 5 (15%). Further literature on the Brockmann method is disclosed in O. A. Neumüller, Römpps Chemie-Lexikon, page 427 (1972).

Other suitable adsorbents are silica gels having specific surface areas of about 500 to about 700 m$^2$/g, and silanized silica gels of about 300 to about 400 m$^2$/g. In the silica gels, the silica is present in the form of highly condensed polysilicic acids having a foliated structure of large surface area. Silica gels wherein the hydrophilic surfaces have been rendered hydrophobic by reaction with chlorosilanes are referred to as silanized silica gels.

The specific surface area is determined by the BET method as disclosed in S. Brunauer, P. H. Emmett and E. Teller, J. Am. Chem. Soc. 60, 309 (1938).

In general, the process according to the present invention is carried out at room temperature (15° to 30°C.), but it can also be advantageous to work at higher temperatures.

The resulting non adsorbed material can be used either directly or after being concentrated to any desired extent, up to freedom from solvent. The adsorbent is, without difficulties, regenerated by means of polar solvents. Suitable polar solvents are methanol, ethanol, propanol, i-propanol, acetone, methylethylketone.

The process according to the invention is used preferentially for the purification of tertiary amines with a total of 6 to 54 carbon atoms in the alkyl groups, which amines result from the thermolysis of tertiary amine hydrochlorides and which are subsequently recycled without removing the solvent. The degree of purity of the purified tertiary amine is above 99%, preferably above 99.5% and especially preferentially above 99.9%.

The examples which follow ilustrate the process according to the invention.

EXAMPLE 1

A mixture of 45 g of tri-(2-ethylhexyl)-amine and 5 g of di-(2-ethylhexyl)-amine hydrochloride, dissolved in 50 g of xylene, is charged onto an adsorption column (diameter 22 mm) which is packed with 225 ml of acidic aluminum oxide (activity level 1, specific surface area 200 m$^2$/g). The eluant employed is 250 ml of xylene.

The eluate which issues contains 44.5 g of tertiary amine which is pure according to gas chromatography. 4.6 g of the secondary amine hydrochloride are isolated by washing the adsorbent with a 1:1 acetone-methanol mixture. The polar solvent mixture is in turn replaced by xylene; a fresh separation of an amine mixture thereupon becomes possible without further regeneration of the adsorbent.

EXAMPLE 2

A mixture of 1,492.5 g of tri-(2-ethylhexyl)-amine and 7.5 g of di-(2-ethylhexyl)-amine hydrochloride, dissolved in 1,500 g of xylene, is separated by means of 225 ml of acidic aluminum oxide (activity level 1, specific surface area 200 m$^2$/g) in an adsorption column according to Example 1, without using additional eluent. 1,270 g of tertiary amine which is pure according to gas chromatography are obtained.

EXAMPLE 3

A mixture of 90 g of tri-(2-ethylhexyl)-amine, 10 g of di-(2-ethylhexyl)-amine and 1 g of 2-ethylhexylamine, dissolved in 100 g of xylene, is separated in accordance with the description of Example 2. 81 g of tertiary amine which is pure according to gas chromatography are isolated before secondary and primary amine are encountered in the non adsorbed material.

EXAMPLE 4

A mixture of 200 g of tri-(2-ethylhexyl)-amine and 4 g of di-(2-ethylhexyl)-amine, dissolved in 200 g of xylene, is separated over 225 ml of silanized silica gel (specific surface area 335 m$^2$/g) in accordance with the description of Example 2. 115 g of tertiary amine which is pure according to gas chromatography are obtained before secondary amine is encountered in the non adsorbed material.

EXAMPLE 5

A mixture of 200 g of tri-(2-ethylhexyl)-amine and 4 g of di-(2-ethylhexyl)-amine, dissolved in 200 g of xylene, is separated over 225 ml of silica gel of specific surface area 700 m$^2$/g in accordance with the description of Example 2. 100 g of tertiary amine which is pure according to gas chromatography are obtained before secondary amine is encountered in the non adsorbed material.

EXAMPLE 6

A mixture of 200 g of tri-(2-ethylhexyl)-amine and 4 g of di-(2-ethylhexyl)-amine, dissolved in 200 g of xylene, is separated over 225 ml of silica gel of specific surface area 500 m$^2$/g in accordance with the description of Example 2. 60 g of tertiary amine which is pure according to gas chromatography are obtained before secondary amine is encountered in the non adsorbed material.

EXAMPLE 7

A mixture of 1,492.5 of trioctylamine and 7.5 g of dioctylamine, dissolved in 1,500 g of xylene, is separated over 225 ml of acidic aluminum oxide (activity level 1, specific surface area 200 m$^2$/g) in accordance with the description of Example 2. 1,190 g of tertiary amine which is pure according to gas chromatography are obtained before secondary amine is encountered in the non adsorbed material.

EXAMPLE 8

A mixture of 180 g of triethylamine and 20 g of diethylamine, dissolved in 200 g of xylene, is separated over 225 ml of acidic aluminum oxide (activity level 1, specific surface area 200 m$^2$/g) in accordance with the description of Example 2. 110 g of tertiary amine which is pure according to gas chromatography are obtained before secondary amine is encountered in the non adsorbed material.

EXAMPLE 9

A mixture of 180 g of trioctylamine and 20 g of dioctylamine is separated over 225 ml of acidic aluminum oxide (activity level 1, specific surface area 200 m$^2$/g) in accordance with the description of Example 2. 105 g of tertiary amine which is pure according to gas chromatography are isolated before secondary amine is encountered in the material leaving the adsorption column.

EXAMPLES 10 AND 11

A mixture of 100 g of trilaurylamine and 500 g of dilaurylamine or 100 g of tristearylamine and 500 g of distearylamine is suspended in xylene to effect a preliminary separation. Hereupon, the tertiary amines dissolve quantitatively, while the secondary amines dissolve to the extent of at most 5%.

For complete removal of the secondary amine, the filtrate is treated, in the manner described, with 225 ml of acidic aluminum oxide of specific surface area 200 m$^2$/g. The non adsorbed material in each case contains the tertiary amines which according to analysis by thin layer chromatography are free from secondary amines.

EXAMPLE 12

Per hour, a mixture of 150 g of trioctylamine and 0.5 g of dioctylamine, dissolved in 600 g of dodecane, the mixture originating from the thermal cleavage of amine hydrochlorides, is passed continuously through an adsorption column (diameter 100 mm) packed with 8 kg of acidic aluminum oxide (activity level 1, specific surface area 200 m$^2$/g). The mixture which issues remains free from secondary amine for about 800 hours.

We claim:

1. A method of purifying impure tertiary amines by separating them from primary and secondary amines and/or their hydrochloride impurities resulting from the preparation of said tertiary amines, comprising, passing said tertiary amines over an adsorbent selected from the group consisting of
   (a) aluminum oxide having a specific surface area of about 100 to 400 m$^2$/g;
   (b) silica gel having a specific surface area of about 500 to 700 m$^2$/g;
   (c) silanized silica gel having a specific surface area of about 300 to 400 m$^2$/g; where specific surface area is measured according to the BET method and thereby moving said primary and secondary amines and/or their hydrochloride impurities and separating pure tertiary amines.

2. The method of claim 1, wherein said tertiary amines being purified are dissolved in a non-polar organic solvent.

3. The method of claim 2, wherein said pure tertiary amines are separated from said solvent.

4. The method of claim 3, wherein said impurities are removed from said adorbents by washing with a polar solvent.

5. The method of claim 2, wherein the tertiary amine being purified originates from the thermolysis of tertiary amine hydrochlorides.

6. The method of claim 3, wherein said pure tertiary amines are separated from said non-polar organic solvent by rectification.

7. The method of claim 1, wherein said pure tertiary amines are selected from the group consisting of tri-(2-ethylhexyl) amine contaminated with di-(2-ethylhexyl)-amine hydrochloride; tri(2-ethylhexyl)-amine contaminated with di(2-ethylhexyl)-amine and 2-ethylhexylamine; tri-(2-ethylhexyl)-amine contaminated with di-(2-ethylhexyl)-amine; trioctylamine contaminated with dioctylamine; triethylamine contaminated with diethylamine; trilaurylamine contaminated with dilaurylamine; trihexylamine contaminated with dihexylamine; tridecylamine contaminated with didecylamine; trimyristylamine contaminated with dimyristylamine; tricetylamine contaminated with dicetylamine; and tristearylamine contaminated with distearylamine.

8. The method of claim 1 wherein said pure tertiary amines comprise a tertiary amine purity of more than about 80%.

9. The method of claim 2, having an amine/non-polar organic solvent ratio of about 1:1 to about 1:10.

10. The method of claim 9, wherein said non-polar organic solvent is selected from the group consisting of hexane, heptane, octane, iso-octane, nonane, decane, undecane, dodecane, tetradecane, cyclohexane, methylcyclohexane, decalin, tetralin, benzene, toluene, cumene, xylenes, cymenes, ethylbenzene, p-tert.-butyltoluene, trimethylbenzenes, 1,2,4-triethylbenzene, 1,3,5-triethylbenzene, tert.-butyl-m-xylene, 1,2,3,4-tetramethylbenzene 1,2,3,5-tetramethylbenzene, 3-phenylpentane and dodecylbenzene.

11. The method of claim 4, wherein said polar solvent is selected from the group consisting of methanol, ethanol, propanol, i-propanol, acetone and methylethylketone.

12. The method of claim 11, wherein the degree of purity of said pure tertiary amines is more than about 99%.

* * * * *